(12) United States Patent
Mah

(10) Patent No.: US 8,478,698 B1
(45) Date of Patent: Jul. 2, 2013

(54) METHODS AND SYSTEMS FOR EMPLOYING ARTIFICIAL INTELLIGENCE IN AUTOMATED ORTHODONTIC DIAGNOSIS AND TREATMENT PLANNING

(76) Inventor: James Mah, Las Vegas, NV (US)

( * ) Notice: Subject to any disclaimer, the term of this patent is extended or adjusted under 35 U.S.C. 154(b) by 587 days.

(21) Appl. No.: 12/726,327

(22) Filed: Mar. 17, 2010

(51) Int. Cl.
*G06F 15/18* (2006.01)
(52) U.S. Cl.
USPC ............................................................. 706/12
(58) Field of Classification Search
None
See application file for complete search history.

(56) References Cited

U.S. PATENT DOCUMENTS 7,991,485 B2 *   8/2011   Zakim ............................... 700/2
2002/0026105 A1 *   2/2002   Drazen ......................... 600/300

OTHER PUBLICATIONS

Hassan Noroozi, "Othodontic Treatment Planning Software", Jul. 2005, American Journal of Orthodontics and Dentofacial Orthopedics, vol. 129 No. 6, pp. 834-837.*
Ahmed El-Baily, "Towards a Complete Computer Dental Treatment System", 2008, IEEE, pp. 1-8.*

* cited by examiner

*Primary Examiner* — Jeffrey A. Gaffin
*Assistant Examiner* — Paulinho E Smith

(57) ABSTRACT

The methods and systems generally entail the use of a server that is configured to receive patient data through a website. The methods and systems further include the use of a database that has access to (i) information derived from textbooks and scientific literature and (ii) dynamic results derived from ongoing and completed patient treatments. The methods and systems further include the operation of at least one computer program within the server, which is capable of analyzing the patient data and identifying at least one diagnosis of the orthodontic condition. The methods and systems further entail assigning a probability value to the at least one diagnosis, with the probability value representing a likelihood that the diagnosis is accurate. The methods and systems further include instructing the computer program to identify at least one treatment approach, a corrective appliance, or a combination thereof for the at least one diagnosis.

12 Claims, 5 Drawing Sheets

Root Tip Analysis (Degrees)

| Tooth # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Mesial |   |   |   |   |   |   |   | 2 | 2 |   |   |   |   |   |   |   |
| Distal |   |   |   |   | 5 |   |   |   |   |   |   |   | 8 |   |   |   |

| Tooth # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Mesial |   |   |   |   |   |   |   | 2 | 2 |   |   |   |   |   |   |   |
| Distal |   |   |   |   |   | 2 |   |   |   |   | 2 |   |   |   |   |   |

FIGURE 3

Tooth Torque Analysis (Degrees)

| Tooth # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Positive |  |  |  |  |  |  | 10 | 10 | 10 | 10 |  |  |  |  |  |  |
| Negative |  |  |  |  |  |  |  |  |  |  |  |  |  |  |  |  |

| Tooth # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Positive |  |  |  |  |  |  |  |  |  |  |  |  |  |  |  |  |
| Negative |  |  |  |  |  |  |  |  |  |  |  |  |  |  |  |  |

FIGURE 4

Arch Length Analysis (Millimeters)

| | Right "E" Space | Right Leeway Space | Right Posterior | Right Anterior | Left Anterior | Left Posterior | Left "E" Space | Left Leeway Space |
|---|---|---|---|---|---|---|---|---|
| Maxilla | | | 1 | 2 | 1 | 1 | | |
| Mandible | | | 1 | 3 | 2 | 1 | | |

FIGURE 5

METHODS AND SYSTEMS FOR EMPLOYING ARTIFICIAL INTELLIGENCE IN AUTOMATED ORTHODONTIC DIAGNOSIS AND TREATMENT PLANNING

FIELD OF THE INVENTION

The field of the present invention generally relates to methods and systems that may be used to diagnose an orthodontic condition. More particularly, the field of the present invention relates to methods and systems for automatically diagnosing, and proposing a treatment for, an orthodontic condition, which methods and systems employ the use of artificial intelligence capabilities.

BACKGROUND OF THE INVENTION

Many systems and methods have been developed or, more typically, envisioned which, hypothetically, could automate the capture of patient data and diagnosis of an orthodontic condition. These actual (or contemplated) systems employ certain components and subsystems that may automate the capture of patient data (such as orthodontic images or scans), the transfer of such data to an orthodontist, and/or even the interpretation of such data (or, more typically, discrete portions of such data). However, the currently-available methods and systems fail to comprise an ability to make decisions based on interpreted data, in an automated fashion. In other words, the currently-available methods and systems do not comprise an effective, accurate, and efficient "artificial intelligence" capability, in the automated diagnosis and treatment of an orthodontic condition.

The present invention addresses these shortcomings of the currently-available systems for automated orthodontic diagnosis and treatment.

SUMMARY OF THE INVENTION

According to certain aspects of the present invention, methods and systems for diagnosing and identifying a treatment for an orthodontic condition are provided. Such methods and systems generally comprise the use of a server on which a centralized website is hosted. The server is configured to receive patient data through the website, with such patient data comprising patient photographs, study models, radiographs, and/or combinations thereof. The methods and systems further comprise the use of a database that includes or has access to (i) information derived from textbooks and scientific literature and (ii) dynamic results derived from ongoing and completed patient treatments.

The invention provides that at least one computer program will operate within the server, which is capable of analyzing the patient data and identifying at least one diagnosis of the orthodontic condition (based on the information derived from textbooks and scientific literature, dynamic results derived from ongoing and completed patient treatments, or combinations thereof). The methods and systems further comprise assigning a probability value to at least one diagnosis, with the probability value representing a likelihood that the diagnosis is accurate. According to such embodiments, the methods and systems of the invention further comprise instructing the computer program to identify at least one treatment approach, a corrective appliance, or a combination thereof for the at least one diagnosis.

The above-mentioned and additional features of the present invention are further illustrated in the Detailed Description contained herein.

BRIEF DESCRIPTION OF THE FIGURES

FIG. 3: a table summarizing the results of a root tip analysis of a patient.

FIG. 4: a table summarizing the results of a tooth torque analysis of a patient.

FIG. 5: a table summarizing the results of an arch length analysis of a patient.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

Figure 1:
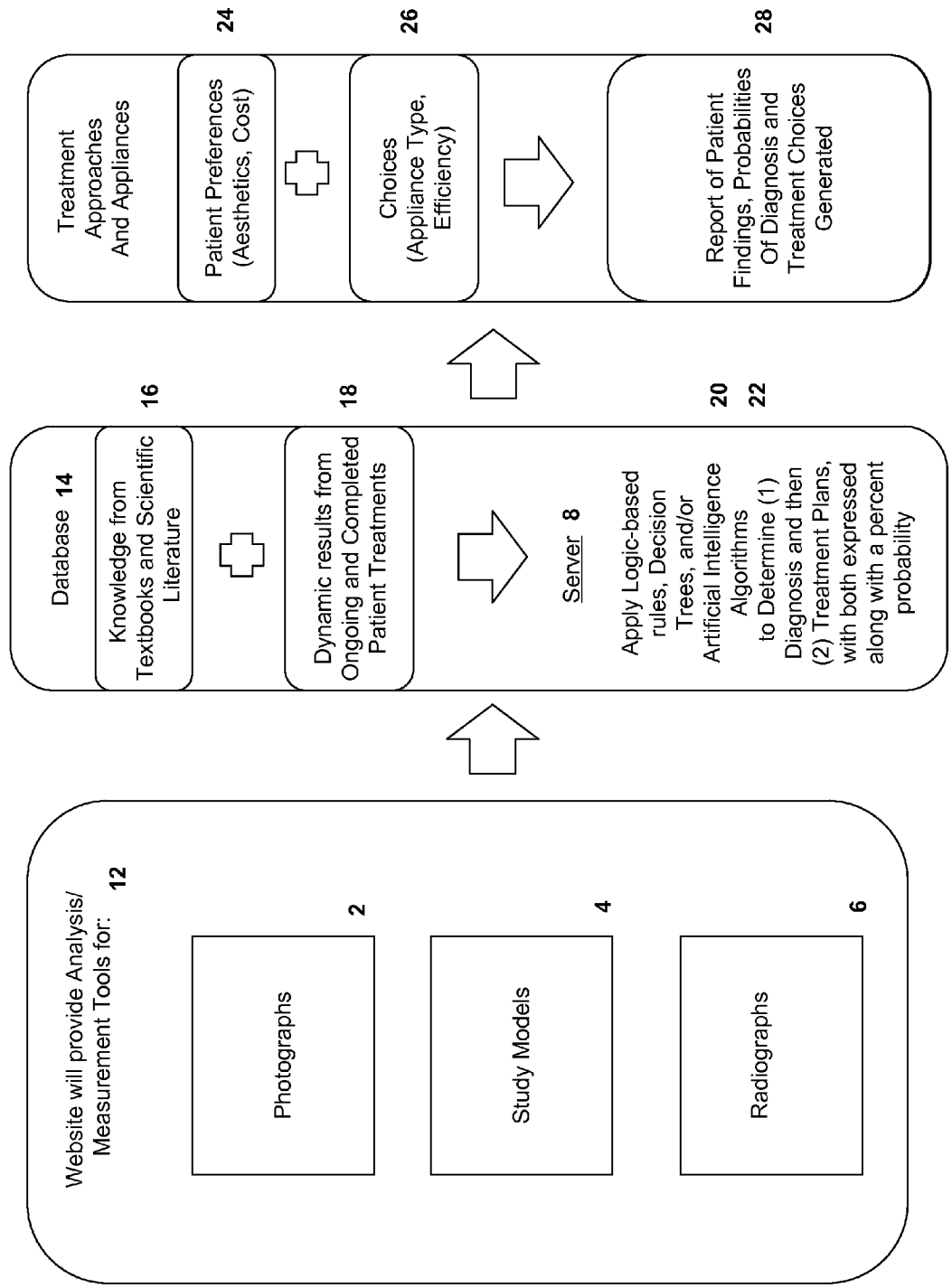
FIG. 1: a diagram illustrating the general steps and processes encompassed by the present invention, namely, the generation of patient data, the analysis of such data by one or more servers, and the automated diagnosis of an orthodontic condition and the proposed treatment approaches therefor.

Referring to FIG. 1, according to certain embodiments of the present invention, automated diagnosis of an orthodontic condition begins with the production of patient-specific data, which may comprise patient photographs 2, study models 4, radiographs 6, and/or combinations thereof. The types of data captured for a particular patient may be the same for all patients, or may be customized for each patient. The "orthodontic condition," referenced herein, may generally comprise an arrangement of a patient's teeth that is undesirable according to applicable orthodontic standards, whereby such arrangement may be undesirable for medical, orthodontic, aesthetic, and other reasons. Examples of such orthodontic conditions include, but are not limited to, overbites, crossbites, openbites, overjets, underbites, and the like.

Figure 2:
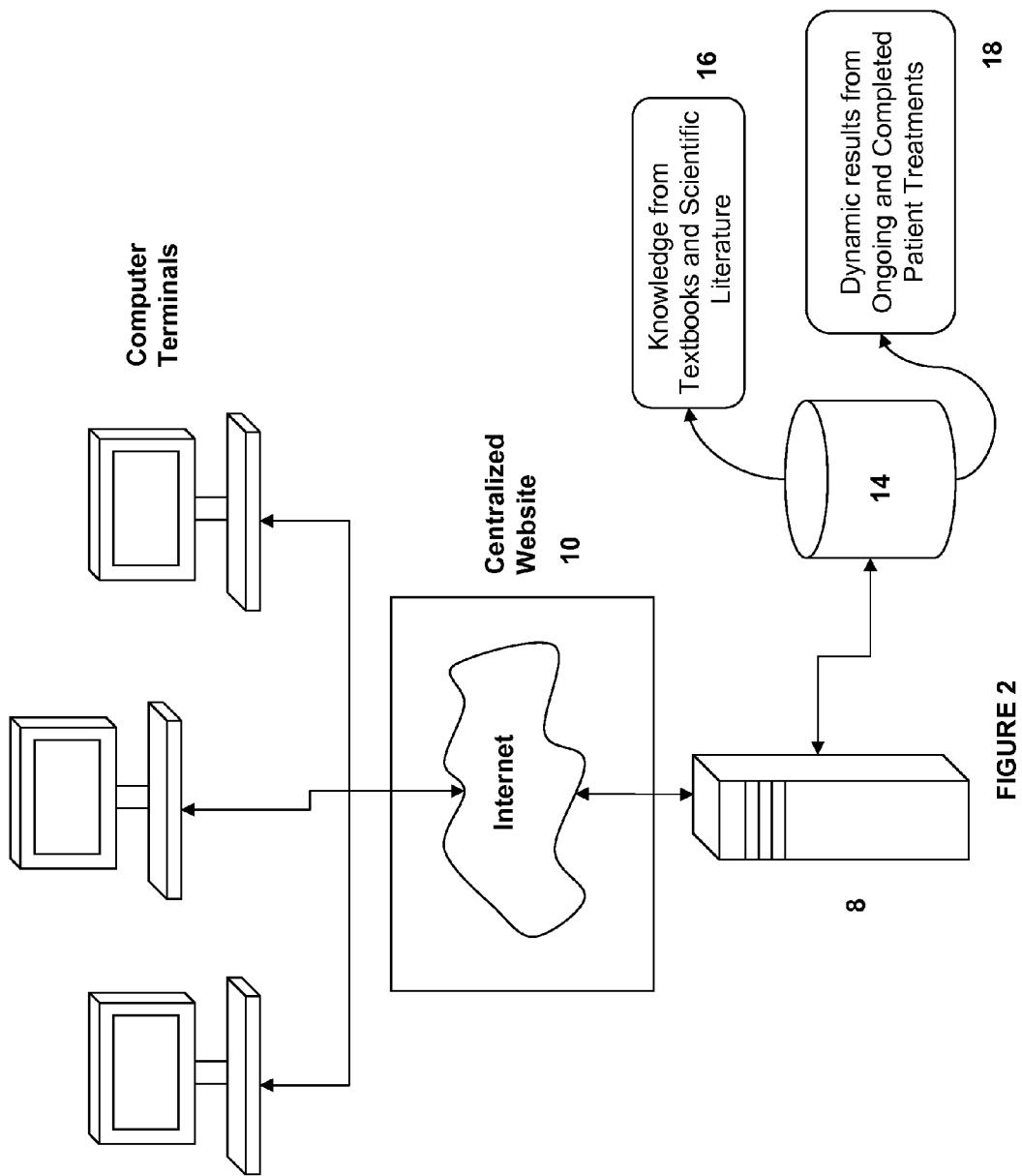
FIG. 2: a diagram illustrating the various components of the systems described herein, namely, the centralized website, server, and database described herein.

These patient data may then be provided to a server 8 through a centralized website 10. Referring to FIG. 2, such data may be provided to the server 8 vis-à-vis an on-line form (within a centralized website 10) through which the data may be uploaded and transferred to the server 8, or through a constant data feed through a standard Internet connection. As described herein, the server 8 will preferably comprise certain tools 12 for analysis and interpretation of such data—and for making intelligent and probabilistic diagnosis and proposed treatments for an orthodontic condition.

The invention provides that the server 8 will preferably be capable of communicating with at least one database 14 (or group of databases). The database 14 will preferably store and/or have access to knowledge and information derived from scientific, medical, and orthodontic textbooks and literature 16. More particularly, the invention provides that a single database 14 may store all of such information—or, alternatively, it may store portions of such information and the server 8 may have access to additional information that may be stored within other databases.

According to certain preferred embodiments, the invention will preferably employ a systematic approach to evaluating the strength of scientific evidence that may be retrieved from the database 14 described herein, for the purpose of diagnosing an orthodontic condition (as described below). For example, the server 8 may consider the quality, quantity and consistency of the evidence to derive a grade or confidence level of the available knowledge. The invention provides that various criteria, such as indirect supporting evidence, may be taken into account in assessing the strength of each piece of scientific evidence. The scientific evidence may then be ranked, based on the grade levels (or confidence levels) assigned thereto.

More particularly, for example, the invention may consider the strongest evidence (i.e., evidence of higher grade levels) being derived from at least one systematic review of one or more well-designed and randomized controlled trials. The invention provides that a second highest grade may be assigned to, for example, evidence derived from at least one properly designed randomized controlled trial, which involved an appropriate sample size and statistical power. The invention further provides that a third highest grade may be assigned to evidence derived from well-designed trials, without randomization; a single group pre-post, cohort, time series study; or matched case-controlled studies. Still further, the invention provides that a fourth grade may be assigned to evidence from well-designed, non-experimental studies, carried out by more than one center or research group. A fifth and lowest grade of evidence may consist of opinions of respected authorities (which are based on clinical evidence), and/or descriptive studies or reports of expert committees.

The invention provides that the database 14 will further comprise, or have access to, information that represents dynamic results from ongoing and previously completed orthodontic studies 18. Preferably, these dynamic results 18 will be organized by orthodontic condition, such that the most relevant information may be retrieved as quickly as possible, within the database 14. Similar to the information derived from scientific, medical, and orthodontic textbooks and literature 16, the invention provides that all of the dynamic results 18 may be stored within the database 14 or, alternatively, portions thereof may be stored within the database 14 and other dynamic results 18 may be retrieved, as needed, from third party databases.

Upon providing the server 8 with the patient data, e.g., patient photographs 2, study models 4, radiographs 6, and/or combinations thereof, a user may instruct the server 8 to conduct an automated diagnosis. The automated diagnosis will be based upon the patient data, the information derived from scientific textbooks and literature 16, and dynamic results from ongoing and previously completed orthodontic studies 18. The server 8 will preferably employ the use of logic-based rules and decision trees 20 to diagnose an orthodontic condition based on all of such information. The invention provides that the server 8 will preferably express the diagnosis by identifying one or more orthodontic conditions, along with a probability value for each orthodontic condition. According to such embodiments, the probability value would represent the relative probability that the diagnosis is accurate.

Still further, the server 8 will be configured to output (recommend) one or more treatment approaches and/or corrective orthodontic appliances 22. More particularly, for each diagnosis 20 identified by the server 8, the server 8 will propose one or more treatment approaches, corrective appliances, or combinations thereof 22. The invention provides that each such proposed treatment approach and corrective appliance will be correlated with a probability value. The invention provides that this probability value will represent the probability of the proposed treatment approach and/or appliance correcting the diagnosed orthodontic condition.

The invention further provides that a user may input patient preferences 24 and/or orthodontist-specified preferences to the server 8 (through the centralized website 10). For example, the invention provides that a patient may filter the proposed treatments and corrective appliance results 26 based on cost, or the relative aesthetics of an appliance. Similarly, an orthodontist may filter the proposed treatments and corrective appliance results 26 based on his/her bias—e.g., an orthodontist may instruct the server 8 to only consider, or to not consider, a certain type of corrective appliance. Upon completion of the foregoing process, the server may be instructed to generate a report 28, which preferably summarizes the patient data, the diagnoses and associated probability values, the proposed treatment approaches and/or corrective devices (and the probability values associated therewith), and any patient and orthodontist preferences that were considered during the analysis.

According to certain embodiments, the invention provides that the server 8 is configured to analyze the patient data by identifying a location and position of a plurality of teeth in the patient data in two-dimensional space or, even more preferably, in three-dimensional space (provided that the type and amount of patient data provided to the server 8 is sufficient to do so). The invention provides that the server 8 may be configured to undertake this analysis automatically or, according to certain embodiments, the centralized website 10 will provide users with certain on-line tools to specify the location and position of the plurality of teeth in the patient data. For example, such on-line tools may be used to identify, within the patient data, the location and position of a patient's incisors, canines, premolars and molars, as shown within the patient data that has been provided to the server 8. The location, position, contours, and size of the plurality of teeth may be mapped out by such user within the centralized website 10, while the user is viewing the patient data that has been uploaded to the server 8, e.g., using a graphics tool that allows a user to, for example, approximately trace or identify the outer boundaries of each tooth.

According to such embodiments, the server 8 may be further configured to assign coordinates to each tooth within the plurality of teeth. The invention provides that such coordinates are preferably correlated to the location and position of each tooth, as automatically determined by the server (or as otherwise identified by a clinician, using the on-line patient data analysis tools, described above). According to these embodiments, the invention provides that the coordinates for each of the plurality of teeth may then be compared (by the server 8) to a table contained within the database 14. The table will preferably comprise a series of diagnostic data sets, with each diagnostic data set comprising coordinates, or a range of coordinates, which are correlated with (1) a known location and position of a plurality of teeth and (2) a previously diagnosed orthodontic condition (which previous diagnoses are derived from (a) information derived from textbooks and scientific literature and (b) dynamic results derived from ongoing and completed patient treatments).

According to such embodiments, the server 8 may then be instructed to identify a diagnostic data set contained within the database 14 that represents a statistical "best fit," or most closely resembles, the coordinates for the plurality of teeth of the patient. At this point, the server 8 may be instructed to diagnosis the orthodontic condition based on the "best fit" diagnostic data set that it identified. As mentioned above, the server 8 may further assign a probability value to this diagnosis. The probability value will preferably be based, at least in part, on a confidence level that has been assigned to the diagnostic data set which the server identifies as the statistical best fit for the coordinates for the plurality of teeth of the patient. This confidence level will preferably be influenced by the grade level that is assigned to the evidence that supports a connection between the orthodontic condition that is correlated with the particular diagnostic data set, as described above.

According to certain embodiments, the server 8 or, more particularly, the computer program housed therein, may be instructed to identify at least one treatment approach, a corrective appliance, or a combination thereof for the at least one diagnosis that is derived from the patient's data. This step may be carried by, for example, instructing the server 8 to calculate a set of target coordinates, which represent a desired and corrected location and position of each tooth in the plurality of teeth of the patient. Based on the target coordinates, the current location and position coordinates of the patient's teeth, and the diagnosed orthodontic position, the server 8 may be instructed to identify at least one treatment approach, a corrective appliance, or a combination thereof, which will be effective to reorient the plurality of teeth towards the location and position represented by the target coordinates. The server 8 may further be instructed to calculate a probability value that is correlated with a relative likelihood of the at least one treatment approach, corrective appliance, or a combination thereof, being effective to reorient the plurality of teeth to a location and position represented by the target coordinates.

According to certain preferred embodiments, the invention will preferably employ certain additional algorithms in analyzing patient data, diagnosing orthodontic conditions and probability values therefor, and proposing treatment approaches and corrective appliances (and probability values therefor). By way of illustration, as mentioned above, the server 8 may be configured to assign greater value (weight) to existing scientific and medical knowledge, relative to dynamic results from ongoing and completed treatments—when diagnosing and providing recommended treatment protocols for patients. The following will describe certain non-limiting examples of algorithms, which may be employed in the processes and systems of the present invention.

The invention provides that artificial intelligence algorithms will preferably be employed in order to create an artificial neural network, which will enable the server to perform the orthodontic diagnosis, treatment planning and prognostication steps described herein. The algorithms may utilize statistical estimation, optimization and control theory methodology, or combinations thereof. In the case of statistical estimation methods, estimators and estimation methods that may be employed include, but are not limited to, the following: maximum likelihood estimators, Bayes estimators, method of moments estimators, Cramer-Rao bound, minimum mean squared error (also known as Bayes least squared error), maximum a posteriori, minimum variance unbiased estimator, best linear unbiased estimator, unbiased estimators, particle filter, Markov chain Monte Carlo, Kalman filter, Ensemble Kalman filter, and Wiener filter. The statistical optimization techniques that may be utilized include single-variable optimizations or, more preferably, multi-variable optimization techniques. The statistical optimization methods may include, but are not limited to, the following: Bundle methods, Conjugate gradient method, Ellipsoid method, Frank-Wolfe method, Gradient descent (also known as steepest descent or steepest ascent), Interior point methods, Line search, Nelder-Mead method, Newton's method, Quasi-Newton methods, Simplex method and Sub-gradient method.

Because the systems and methods of the present invention involve certain input provided by users of the invention, the systems and methods are dynamic. As such, the invention provides that algorithms that employ control theory may be employed to solve problems in connection with the orthodontic diagnosis, treatment planning and prognostication steps described herein. Non-limiting examples of such control theory methods include: Adaptive control, Hierarchical control, Intelligent control, Optimal control, Robust control and Stochastic control.

EXAMPLES

Example of Optimization Algorithm for Decision Making in Diagnosis and Treatment Planning.

An important aspect of multiple optimization is the handling of human preferences, such as the type of cost-and aesthetic-related preferences that a patient or orthodontist may provide to the system described herein. Although selection or prioritizing alternatives from a set of available options with respect to multiple criteria termed Multi-Criteria Decision Making (MCDM) is an effective optimization approach, in practical applications, alternative ratings and criteria weights can not always be precisely assessed due to unquantifiable, incomplete, and/or unobtainable information—or because of a lack of knowledge that may cause subjectiveness and vagueness in decision performance. As such, the invention provides that the application of fuzzy set theory to MCDM models provides an effective solution for dealing with subjectiveness and vagueness commonly found with clinical information. In such embodiments, the invention provides that human preferences—from both patient and clinician-may be assigned "utility values" in which a scaled real number is assigned to indicate its relative importance. The resulting weighting vector, which evaluates criteria of decision making, is then provided in fuzzy linguistic terms such as very poor, poor, fair, good, and very good.

Example of Decision Tree Algorithm for Decision Making in Diagnosis and Treatment Planning.

The invention provides that a decision tree method referred to as "04.5," which allows for input of continuous numerical data, is preferably employed in the methods and systems described herein. The invention provides that, under this approach, a decision tree may be "learned" vis-a-vis splitting a source set into subsets, based on an attribute value test. The invention provides that this process may be repeated on each derived subset in a recursive manner, which is completed when the subset (at a node) has the same value of the target variable, or when splitting no longer adds value to predictions. According to this embodiment, decision trees are used for relatively simpler functions as decision-tree learners create over-complex trees (overfitting), although pruning may, optionally, be performed to minimize this problem. In addition, concepts that are relatively more difficult to learn are not easily expressed by decision trees-and, in such case, more advanced algorithms will be implemented in the systems and methods described herein.

Example of Partially Observable Markov Decision Processes (POMDPs) and Variants Thereof.

The invention provides that POMDPs are preferably used in the clinical applications described herein, particularly for decisions that are made based on incomplete information. The invention provides that POMDPs are preferably advantageous insofar as they facilitate the combination of patient data, e.g., patient data derived from examination, photographs, radiographs and any other diagnostic aids-as well as the current state of knowledge of the cause-and-effect representation from these data and measurements. The invention provides that feature selection may be performed using pattern recognition techniques and, furthermore, the treatment decisions with which to restore the patient to a more desirable or ideal state are produced.

Patient Example.

The following example describes the application of the processes described herein to a patient in need of orthodontic diagnosis and treatment. The process begins with the patient undergoing cephalometric radiographic analysis. The data generated by such analysis are presented in the table below.

| Measurement | Patient |
| --- | --- |
| SNA (degrees) | 82° |
| SNB (degrees) | 74° |
| ANB (degrees) | 8° |
| Maxillary incisor to NA (degrees) | 22° |
| Maxillary incisor to NA (millimeters) | 6 mm |
| Mandibular incisor to NB (degrees) | 24° |
| Mandibular incisor to NB (millimeters) | 4 mm |
| Pogonion to NB (millimeters) | 4 mm |
| Maxillary incisor to Mandibular incisor (degrees) | 140° |
| Occlusal plane to SN (degrees) | 15° |
| Go-Gn to SN (degrees) | 32° |
| Mandibular incisor to MP (degrees) | 86° |

Those of ordinary skill in the art will appreciate that the cephalometric radiographic analysis may be performed to capture measurements, other than those specified above. However, the measurements summarized in the table above are often important to any orthodontic diagnosis. Next, the patient's dentition may be analyzed and measured. The table below provides a summary of the results of such analysis and, specifically, the analysis of the patient's anteroposterior and vertical movements.

| Anteroposterior Movements (mm) | | | | | |
| --- | --- | --- | --- | --- | --- |
| | Right Molar | Right Canine | Midline | Left Canine | Left Molar |
| Maxilla | | | 1.5 mm left | 1.0 distal | |
| Mandible | 3 mesial | 2.5 mesial | 0.5 mm left | 2 mesial | 3 mesial |

| Vertical Movements (mm) | | | | | |
| --- | --- | --- | --- | --- | --- |
| | Right Molar | Right Canine | Midline | Left Canine | Left Molar |
| Maxilla | | 1.5 mm occlusal | | 2.0 mm occlusal | |
| Mandible | | | | | |

| Curve of Spee (mm) | |
| --- | --- |
| Maxilla | |
| Mandible | 3 mm |

The diagnostic process of this Example further entails the following analyses of the patient: (1) a root tip analysis (results are summarized in FIG. 3); (2) a tooth torque analysis (results are summarized in FIG. 4); (3) an arch length analysis (results are summarized in FIG. 5); and (4) a Bolton analysis (the results of which are summarized in the table below).

| Bolton Analysis (Millimeters) | | |
| --- | --- | --- |
| | Anterior (Bolton 6) mm | Posterior (Bolton 12) mm |
| Maxilla Mandible | 2 mm deficient | 2 mm deficient |

The invention provides that a series of image analyses may then be performed, namely, an image analysis of a patient's frontal and profile planes.

The results captured in this Example are summarized in the tables below.

| Frontal Analysis | |
| --- | --- |
| Parameter | Results |
| Upper Third | Within normal limits |
| Middle Third | Within normal limits |
| Lower Third | Decreased |
| Maxillary Lip | Within normal limits |
| Mandibular Lip | Within normal limits |
| Smile | Within normal limits |
| Gingival Display | Within normal limits |
| Symmetry | Within normal limits |

| Profile Analysis | |
| --- | --- |
| Parameter | Results |
| Profile | Convex |
| Maxillary lip to E plane | 1 mm |
| Lip strain | Yes |
| Lip competence | Incompetent |

As explained above, the invention provides that a patient and/or clinician (dentist or orthodontist) may specify certain additional criteria, which the server will consider in calculating a diagnosis and treatment plan. The table below provides the criteria selected by the patient in this Example.

| Patient Preferences | |
| --- | --- |
| Parameter | Priority (Scale of 1-10 for Importance) |
| Facial Aesthetics | 9 |
| Comfort | 2 |
| Treatment Time | 7 |
| Removable Appliances | 1 |
| Aesthetic Braces | 2 |
| Orthognathic Surgery | 1 |
| Cost | 5 |

The foregoing patient data, measurements, and preferences are subsequently provided to the server, via the centralized website described herein. Using one or more artificial intelligence algorithms, such as the algorithms described herein (or combinations thereof), as well as (i) information derived from textbooks and scientific literature and (ii) dynamic results derived from ongoing and completed patient treatments, the server calculates one or more diagnoses for the patient, along with an associated probability value (which is indicative of the relative accuracy of each diagnosis). Three diagnoses, and associated probability values, for this Example are listed below.

Diagnosis One: Class II Malocclusion (85%)
Diagnosis Two: Class I Malocclusion (14%)
Diagnosis Three: Class III Malocclusion (1%)

In addition, based on the foregoing patient data, measurements, preferences, information, and diagnoses, the server calculates one or more proposed treatment regimens for the patient, along with a probability value that is correlated with a relative likelihood of the relevant treatment approach, corrective appliance, or a combination thereof, being effective to reorient the patient's teeth to the desired location and position. The list of proposed treatment regimens, and corresponding probability values, calculated in this Example is provided below.

Growth Modification (61%)
Mandibular Extractions (72%)
Maxillary Extractions (58%)
Removable Appliances (8%)
Fixed Appliances (92%)
Retainers (99%)

In this Example, the server further calculated the average probably treatment time to be about 26.5 months.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for diagnosing and identifying a treatment for an orthodontic condition, which comprises:
    (a) providing a server on which a centralized website is hosted, wherein the server is configured to receive patient data through the website, wherein the server is configured to identify a location and position of a plurality of teeth in the patient data in three-dimensional space;
    (b) providing a database that comprises or has access to (i) information derived from textbooks and scientific literature and (ii) dynamic results derived from ongoing and completed patient treatments;
    (c) operating at least one computer program within the server, which is capable of analyzing the patient data and identifying at least one diagnosis of the orthodontic condition based on said information derived from textbooks and scientific literature and dynamic results derived from ongoing and completed patient treatments, wherein identifying at least one diagnosis of the orthodontic condition is performed by:
        (i) assigning coordinates to each tooth within the plurality of teeth, wherein said coordinates are correlated to a location and position of each tooth;
        (ii) comparing the coordinates for each of the plurality of teeth to a table contained within the database, wherein the table comprises a series of diagnostic data sets with each diagnostic data set comprising coordinates, or a range of coordinates, which are correlated with (y) a known location and position of a plurality of teeth and (z) a previously diagnosed orthodontic condition;
        (iii) instructing the server to identify a diagnostic data set contained within said database which represents a statistical best fit, or most closely resembles, the coordinates for the plurality of teeth of the patient; and (iv) instructing the server to diagnosis the orthodontic condition based on the diagnostic data set identified in step (c)(iii);
    (d) assigning a probability value to the at least one diagnosis, wherein the probability value represents a likelihood that the diagnosis is accurate; and
    (e) instructing the computer program to identify at least one treatment approach, a corrective appliance, or a combination thereof for the at least one diagnosis.

2. The method of claim 1, wherein the probability value that is assigned to the at least one diagnosis is based, at least in part, on a confidence level that has been assigned to the diagnostic data set which the server identifies as the statistical best fit for the coordinates for the plurality of teeth of the patient.

3. The method of claim 2, which further comprises instructing the computer program to identify at least one treatment approach, a corrective appliance, or a combination thereof for the at least one diagnosis, by instructing the server to:
    (a) calculate a set of target coordinates, which represent a desired and corrected location and position of each tooth in the plurality of teeth of the patient; and
    (b) identify at least one treatment approach, a corrective appliance, or a combination thereof, which will be effective to reorient the plurality of teeth towards a location and position represented by the target coordinates.

4. The method of claim 3, which further comprises instructing the server to calculate a probability value that is correlated with a relative likelihood of the at least one treatment approach, corrective appliance, or a combination thereof, being effective to reorient the plurality of teeth to a location and position represented by the target coordinates.

5. The method of claim 4, wherein the step of identifying at least one diagnosis of the orthodontic condition employs an application of at least one artificial intelligence algorithm.

6. The method of claim 5, wherein the step of identifying at least one treatment approach, a corrective appliance, or a combination thereof for the at least one diagnosis, employs an application of at least one artificial intelligence algorithm.

7. A system for diagnosing and identifying a treatment for an orthodontic condition, which comprises:
    (a) a server on which a centralized website is hosted, wherein the server is configured to (i) receive patient data through the website; (ii) identify a location and position of a plurality of teeth in the patient data in three-dimensional space; and (iii) assign coordinates to each tooth within the plurality of teeth,
    wherein said coordinates are correlated to the location and position of each tooth;
    (b) a database that comprises or has access to (i) information derived from textbooks and scientific literature and (ii) dynamic results derived from ongoing and completed patient treatments; and
    (c) at least one computer program housed within or accessible by the server, which is capable of analyzing the patient data and identifying at least one diagnosis of the orthodontic condition based on said information derived from textbooks and scientific literature and dynamic results derived from ongoing and completed patient treatments, wherein the computer program is configured to identify at least one diagnosis of the orthodontic condition by:
        (i) comparing the coordinates for each of the plurality of teeth to a table contained within the database, wherein the table comprises a series of diagnostic data sets with each diagnostic data set comprising coordinates, or a range of coordinates, which are correlated with (y) a known location and position of a plurality of teeth and (z) a previously diagnosed orthodontic condition;

(ii) identifying a diagnostic data set contained within said database which represents a statistical best fit, or most closely resembles, the coordinates for the plurality of teeth of the patient; and (iii) diagnosing the orthodontic condition based on the diagnostic data set identified in paragraph (c)(ii); wherein the server is further configured to be capable of: (1) assigning a probability value to the at least one diagnosis, wherein the probability value represents a likelihood that the diagnosis is accurate; and (2) instructing the computer program to identify at least one treatment approach, a corrective appliance, or a combination thereof for the at least one diagnosis.

8. The system of claim 7, wherein the probability value that is assigned to the at least one diagnosis is based, at least in part, on a confidence level that has been assigned to the diagnostic data set which the server identifies as the statistical best fit for the coordinates for the plurality of teeth of the patient.

9. The system of claim 8, wherein the computer program is configured to identify at least one treatment approach, a corrective appliance, or a combination thereof for the at least one diagnosis, by instructing the server to:

(a) calculate a set of target coordinates, which represent a desired and corrected location and position of each tooth in the plurality of teeth of the patient; and (b) identify at least one treatment approach, a corrective appliance, or a combination thereof, which will be effective to reorient the plurality of teeth towards a location and position represented by the target coordinates.

10. The system of claim 9, wherein the server is further configured to calculate a probability value that is correlated with a relative likelihood of the at least one treatment approach, corrective appliance, or a combination thereof, being effective to reorient the plurality of teeth to a location and position represented by the target coordinates.

11. The system of claim 10, wherein the server is configured to employ at least one artificial intelligence algorithm when identifying at least one diagnosis of the orthodontic condition.

12. The system of claim 11, wherein the server is configured to employ at least one artificial intelligence algorithm when identifying at least one treatment approach, a corrective appliance, or a combination thereof for the at least one diagnosis.

\* \* \* \* \*